United States Patent [19]
McMahon et al.

[11] Patent Number: 5,503,139
[45] Date of Patent: Apr. 2, 1996

[54] CONTINUOUS FLOW ADAPTOR FOR A NEBULIZER

[76] Inventors: Michael D. McMahon, 579 S. Hibiscus Way, Anaheim Hills, Calif. 92808; Andre M. Rustad, 12366 Highland Ave., Etiwanda, Calif. 91739

[21] Appl. No.: 190,629

[22] Filed: Feb. 2, 1994

[51] Int. Cl.$^6$ .............................. A61M 11/06; B05B 1/26
[52] U.S. Cl. .............................. 128/200.18; 128/200.21; 239/338
[58] Field of Search .................. 128/200.18, 200.19, 128/200.21, 203.12, 203.16, 203.17, 203.26, 203.27; 239/338, 339, 328, 349, 370, 371, 432

[56] References Cited

U.S. PATENT DOCUMENTS

| | | |
|---|---|---|
| Re. 33,642 | 7/1991 | Lester . |
| Re. 33,717 | 10/1991 | Svoboda . |
| 3,172,406 | 3/1965 | Bird et al. . |
| 3,382,871 | 5/1968 | Parry .................. 128/200.18 |
| 3,572,590 | 3/1971 | Malone . |
| 3,762,409 | 10/1973 | Lester . |
| 3,838,686 | 10/1974 | Szekely . |
| 4,007,238 | 2/1977 | Glenn .................. 128/200.18 |
| 4,048,997 | 9/1977 | Raghavachari et al. . |
| 4,116,387 | 9/1978 | Kremer, Jr. et al. . |
| 4,251,033 | 2/1981 | Rich et al. . |
| 4,429,835 | 2/1984 | Brugger et al. ............. 128/200.18 |
| 4,456,179 | 1/1984 | Kremer . |
| 4,462,397 | 7/1984 | Suzuki . |
| 4,470,412 | 9/1984 | Nowacki et al. . |
| 4,512,341 | 4/1985 | Lester . |
| 4,560,519 | 12/1985 | Cerny .................. 128/200.18 |
| 4,566,452 | 1/1986 | Farr . |
| 4,657,007 | 4/1987 | Carlin et al. . |
| 4,746,067 | 5/1988 | Svoboda . |
| 4,805,609 | 2/1989 | Roberts et al. . |
| 4,852,561 | 8/1989 | Sperry . |
| 4,941,468 | 7/1990 | Giovanni . |
| 4,953,547 | 9/1990 | Poole, Jr. . |
| 5,008,048 | 4/1991 | Ryder . |
| 5,277,175 | 1/1994 | Riggs et al. . |

FOREIGN PATENT DOCUMENTS

| | | |
|---|---|---|
| 0170715 | 2/1986 | European Pat. Off. .......... 128/200.18 |
| 1461679 | 11/1966 | France . |
| 1955545 | 5/1971 | Germany . |
| 548068 | 9/1956 | Italy .................. 128/200.18 |
| 2019743 | 11/1979 | United Kingdom . |

Primary Examiner—Kimberly L. Asher
Attorney, Agent, or Firm—Paul Schaafsma; Francis Kowalik; Paul Flattery

[57] ABSTRACT

A nebulizer (10) has a nebulizer top (12) defining an aerosol outlet (66) and a reservoir bottom (14) defining a liquid reservoir (21) and a threaded connection (38,68) between the reservoir bottom (14) and the nebulizer top (12). A nebulizing structure (24,46) within the nebulizer provides an aerosol to the aerosol outlet (66). A continuous flow adaptor (16) for the nebulizer has a side wall (90) with first and second open ends (94,100) defining a spacer interior. An orifice (116) in the side wall (90) of the adaptor (16) allows for fluid communication with the adaptor (16) interior from outside of the adaptor (16). A luer connector (118) is provided on the side wall (90) of the adaptor (16) for connecting the orifice (116) in fluid tight communication with a fluid supply. The adaptor (16) includes threads (92,98) proximate the first and second open ends (24,100) for cooperatively engaging the threaded portions (38,68) of the reservoir top (12) and reservoir bottom (14).

10 Claims, 2 Drawing Sheets

CONTINUOUS FLOW ADAPTOR FOR A NEBULIZER

BACKGROUND OF THE INVENTION

1. Technical Field

The present invention is directed toward nebulizers for medicating a patient's lungs and, more particularly, to a continuous flow adaptor for a nebulizer.

2. Background Art

Nebulizers are devices for delivering atomized medication to air to be inhaled into the lungs of a patient. A variety of nebulizer structures are known in the medical field. An exemplary nebulizer is that disclosed in Farr, U.S. Pat. No. 4,566,452. Farr discloses a nebulizer having a nebulizer top and reservoir bottom which are threadably connectable. A gas jet extends from the reservoir bottom along a longitudinal axis of the reservoir bottom. A liquid spray nozzle surrounds the gas jet defining a passageway for liquid between the gas jet and the liquid nozzle. At the top of the gas jet is a gas orifice which leads into a space in fluid communication with the liquid nozzle passageway. A liquid orifice in a top of the liquid nozzle is axially aligned with the orifice in the gas jet. A diffuser is connected to the nebulizer top and spaced from the nozzle orifice with the nebulizer top and reservoir bottom threadably connected. As gas is caused to flow through the gas jet, a vacuum is formed in the space between the gas orifice and the nozzle orifice, drawing fluid for nebulization to the fluid nozzle orifice. Nebulized fluid impinges upon the diffuser, causing oversized droplets to stick to the diffuser and providing a finely nebulized mist for delivery to the lungs of a patient.

Nebulizers are often installed in an inhalation circuit of a mechanical ventilator. The ventilator augments respiration of a patient unable to sustain breathing on his own and the nebulizer provides medication applied to the patient's lungs. Nebulizers such as that disclosed in Farr typically have a select volume defined by the size of the reservoir. One problem with such a structure occurs when a patient requires delivery of a volume of nebulized medication in excess of the select volume of the nebulizer reservoir. Using a structure such as that disclosed in Farr typically requires that the reservoir top be detached from the reservoir bottom and additional medication poured into the reservoir. However, this procedure results in depressurizing and a complete loss of function of the ventilator system until the nebulizer top is reattached. In addition, there is a possibility of cross-contamination into and out of the reservoir system. Furthermore, when the nebulizer top is removed from the reservoir bottom, nebulization cannot take place and, therefore, medication cannot reach the patient's lungs. In some cases, particularly with critical care patients, these problems can result in adverse affect upon the patient's treatment. Thus, a structure for allowing continuous refill of the nebulizer reservoir without disconnecting the nebulizer from the inhalation circuit is necessary.

One method of continuously supplying medication to a nebulizer reservoir has been to insert an IV needle through the side of the nebulizer reservoir. This method creates the potential for fluid leaks and introduction of particulate matter into the reservoir, which can result in clogging of the fluid nozzle. In addition, the needle hole presents an avenue for contamination.

A second method which has been used to continuously nebulize a patient is to attach a valve T-piece to the aerosol outlet prior to attaching the nebulizer to the inhalation circuit. Medication may then be introduced through the T-valve into the nebulizer reservoir. This procedure has the serious drawback of lowering the efficiency of the device by passing the added medication through the aerosol stream, resulting in coalescing of aerosol particles into the medication droplets and thereby reducing aerosol output and altering the mean particle size and distribution.

It is also known in the art to provide a liquid inlet in the side wall of nebulizer reservoir. Such an inlet is disclosed in Kremer, U.S. Pat. No. 4,456,179; Robert, U.S. Pat. No. 5,119,807; and Poole, Jr., U.S. Pat. No. 4,953,547. While such structures do allow for continuous feed of medication to a nebulizer reservoir, they are not without serious drawbacks. Most significantly, including such an inlet on every nebulizer increases the cost of manufacturing the nebulizer. Not only is the mold more complicated, but an additional manufacturing step is required to cap the inlet. Thus, nebulizer cost is increased even when the nebulizer will not be required to accommodate continuous feeding of medication. While hospitals could stock nebulizers with or without the reservoir inlet, this would increase shelf space requirements and inventory costs. In addition, the liquid inlet increases the bulk of the nebulizer, therefore making the nebulizers more difficult to package compactly and increasing the shelf space required to store the nebulizers. Particularly in this age of extreme sensitivity in the rising costs of health care, these prior art devices simply do not provide the flexibility necessary to efficiently address the full range of nebulizer requirements.

The continuous flow adaptor disclosed and claimed herein is directed toward overcoming one or more of the problems discussed above.

SUMMARY OF THE INVENTION

Disclosed is a continuous flow adaptor for a nebulizer. The nebulizer with which the adaptor is used has a reservoir bottom, a nebulizer top and a threaded connection between the reservoir bottom and the nebulizer top. The reservoir bottom includes a gas jet extending along a longitudinal axis of the reservoir bottom. A gas inlet means is connected to the gas jet. A liquid spray nozzle in fluid communication with the reservoir is mounted relative to the gas jet for nebulization of liquids sprayed from an outlet of the liquid spray nozzle. The nebulizer top includes a diffuser spaced a critical distance from the liquid spray outlet when the reservoir bottom and top are threadably connected and an aerosol outlet. The continuous flow adaptor includes a side wall between the first and second open ends defining an adaptor interior. An orifice in the side wall allows for fluid communication with the adaptor interior from outside of the adaptor. A luer connector is provided on the side wall for connecting the orifice in fluid tight communication with a fluid supply. Threads proximate the first and second open ends are cooperatively engageable with the threads of the nebulizer top and the reservoir bottom.

In a preferred form of the invention, the continuous flow adaptor includes an adaptor diffuser and a plurality of fibs extending from the side wall of the adaptor for positioning the adaptor diffuser within the adaptor interior at the critical distance from the liquid spray nozzle with the adaptor threadably engaged between the nebulizer top and the reservoir bottom. The diffuser of the nebulizer top resides behind a trailing end of the adaptor diffuser and between the ribs supporting the adaptor diffuser with the adaptor in place between the nebulizer top and reservoir bottom.

The nebulizer adaptor of the present invention provides a structure which can be quickly and easily installed in a hand-held nebulizer to convert a fixed volume nebulizer into a continuous feed nebulizer. The adaptor is configured to cooperatively engage the threadable connection between the reservoir top and reservoir bottom, facilitating quick and easy assembly. The adaptor includes a diffuser which assumes the position of a diffuser in the nebulizer top so that proper nebulizer output and particle size are ensured. The adaptor eliminates the requirement of prior art structures to have a fluid inlet permanently attached to the nebulizer reservoir to facilitate continuous nebulization. In this manner, the adaptor reduces inventory costs by allowing a hospital to stock a single fixed volume nebulizer without a bulky and cost-increasing continuous flow inlet which, through use of the adaptor, can be readily adapted to a continuous flow device. Thus, the continuous flow adaptor of the present invention both reduces product cost, inventory costs and inventory space requirements.

DETAILED DESCRIPTION OF THE PREFERRED EMBODIMENT

A nebulizer (10) includes a nebulizer top (12) and a reservoir bottom (14). A continuous flow adaptor (16) is configured for attachment between the nebulizer top (12) and reservoir bottom (14) in a manner which will be discussed in greater detail below.

Figure 2:
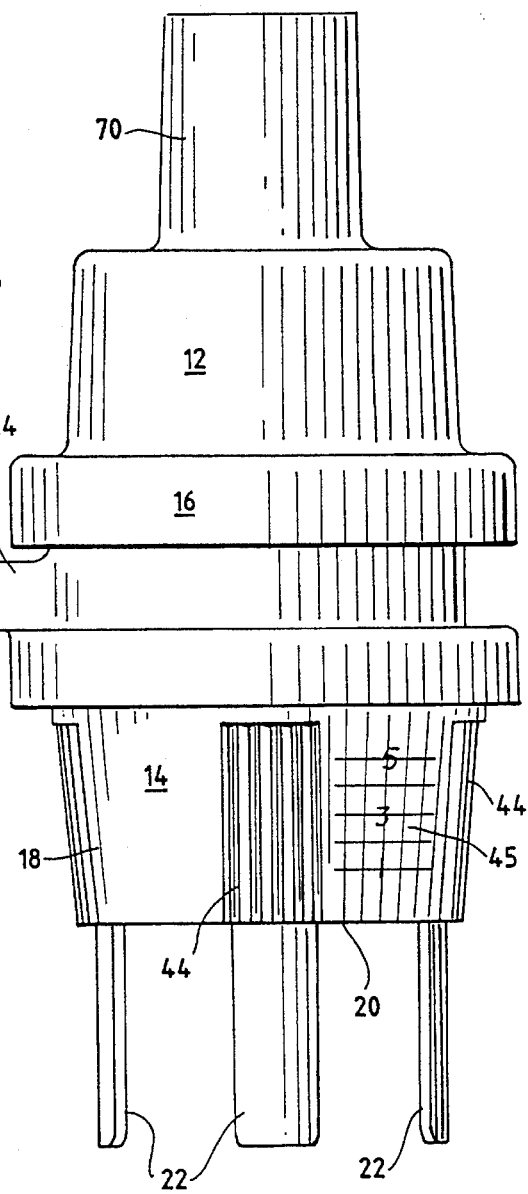
FIG. 2 is an elevation view of a nebulizer with the continuous flow adaptor installed between the nebulizer top and bottom.

The reservoir bottom (14) has a peripheral side wall (18) extending upwardly and outwardly from a bottom wall (20) defining a liquid reservoir (21). Four legs (22) descend from the outside of the bottom wall (20) and maintain the nebulizer (10) in an upright configuration as illustrated in FIG. 2. A gas jet (24) extends along the longitudinal axis (26) of the reservoir bottom (14) through the bottom wall (20). The bottom of the gas jet (24) is a gas inlet (28) connectable to a supply of gas (not shown) through a flexible plastic tube (29). At the top (30) of the gas jet (24) is a gas orifice (31) surrounded by circumferentially spaced axial spacers (32). Circumferentially spaced longitudinal spacers (34) surround the gas inlet jet (24).

Male threads (38) surround the top (40) of the side wall (18). An annular V-shaped channel (42) is in the top (40) of the side wall (18). Undulating ribs (44) extend longitudinally at 90° intervals from the side wall (18) of the reservoir bottom (14). Indicia (45) on the side wall (18) indicate the level of liquid in the reservoir (21).

A liquid spray nozzle (46) envelops the gas jet (24) and is spaced from it axially and radially by the spacers (32) and (34), respectively. The spacers (34) define a nozzle liquid passageway (50) between the spray nozzle (46) and gas jet (24). The nozzle liquid passageway (50) opens to a space (52) maintained between the top (56) of the spray nozzle (46) and the top (30) of the gas jet (24) by the spacers (32). The top (56) of the spray nozzle (46) has a fluid orifice (58) coaxial with the gas orifice (31).

Figure 3:
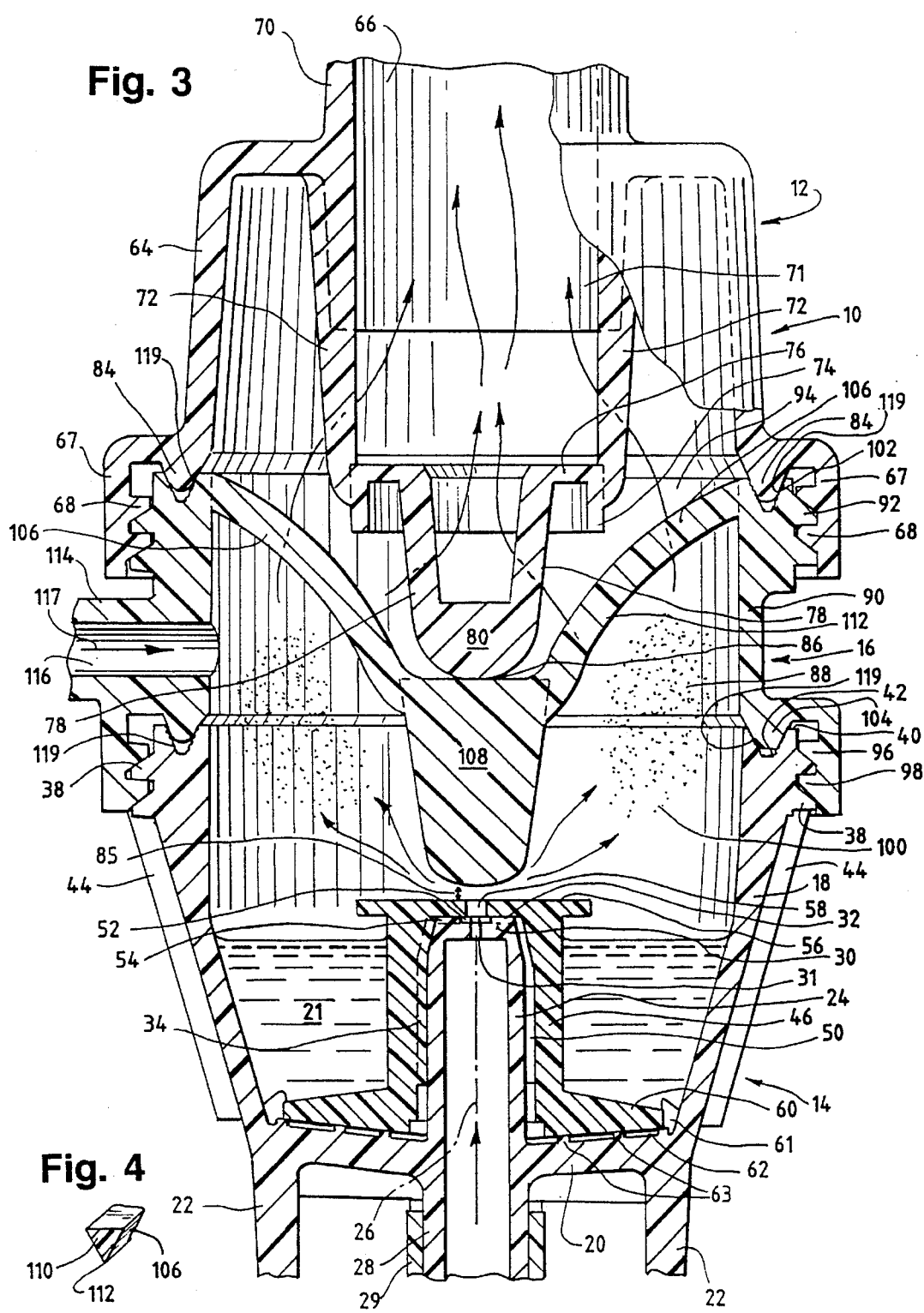
FIG. 3 is a sectional view of the nebulizer including the continuous flow adaptor as shown in FIG. 2.

A collector flange (60) extends around the bottom of the spray nozzle (46) in close proximity to the bottom wall (20) of the reservoir bottom (14). The periphery of the collector flange (60) is secured to the reservoir bottom (14) by radially spaced clips (61). The collector flange (60) is maintained a selected distance from the reservoir bottom wall (20) by spacers (63) extending from the reservoir bottom wall (20) to define a collector flange passageway (62). As seen in FIG. 3, the nozzle liquid passageway (50) and the collector flange passageway (62) are in fluid communication.

Figure 1:
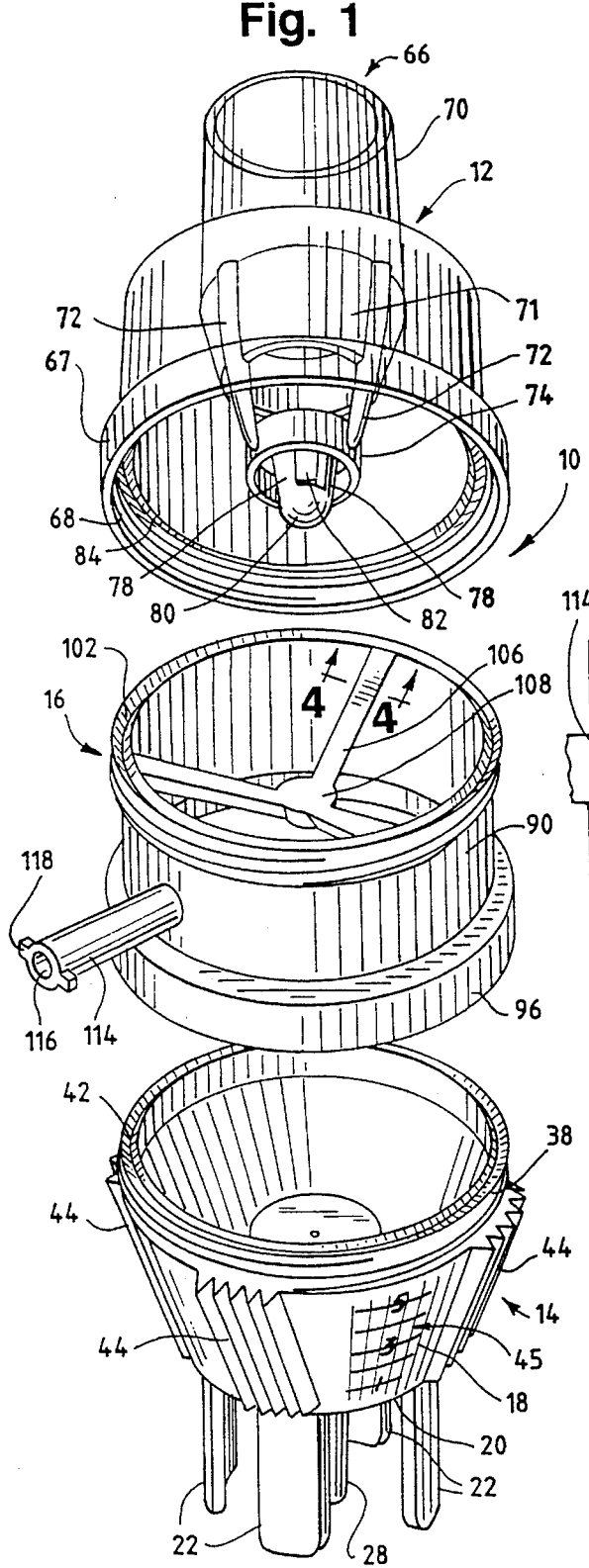
FIG. 1 is an exploded perspective view of a hand-held nebulizer including the continuous flow adaptor of the present invention.

The nebulizer top (12) has a side wall (64) defining at one end an aerosol outlet (66) and at an opposite end a collar (67) having female threads (68) which are configured to threadably engage the male threads (38) of the reservoir bottom (14). A substantially cylindrical wall (70) surrounds the aerosol outlet (66) and is connectable to an inhalation tube of a patient ventilator (not shown) or other structures for conveying nebulized medication from the aerosol outlet to a patient's lungs. A first baffle (71) descends from the aerosol outlet (66). Three legs (72) located 120° apart (two shown) descend from the first baffle (71) and are joined to a second baffle (74). An inwardly extending annular flange (76) extends around the top of the second baffle (74) and a pair of diffuser legs (78) extend downward from the inwardly extending annular flange (76) to support a nebulizer diffuser (80). A pair of longitudinal spaces (82) (one shown in FIG. 1) separate the diffuser legs (78).

An annular V-shaped protrusion (84) extends from the bottom of the nebulizer top (12) just inside of the female threads (68) of the collar (67). With the nebulizer top (12) threadably engaged to the reservoir bottom (14), the annular V-shaped protrusion (84) is nested within the annular V-shaped channel (42) of the nebulizer bottom (14) to form a fluid seal therebetween. Also, with the nebulizer top (12) and the reservoir bottom (14) threadably engaged, the leading surface (86) of the nebulizer diffuser (80) is spaced a distance of about 0.022 inches from the fluid orifice (58) to ensure generation of an aerosol having correct particle size. The diffuser (80) in conjunction with the first and second baffles (71,74) and the inwardly extending annular flange (76) knock out oversize droplets of liquid from the aerosol and return them to the reservoir (14).

In operation, the aerosol outlet (66) is connected to an inhalation line of a ventilator which in turn is connected to a patient's mouthpiece. Compressed gas such as air is supplied through the gas inlet (28) during the inhalation cycle of a patient's breathing, while the compressed air is cut off during the exhalation cycle of the patient's breathing. Compressed air supplied through the air inlet (28) passes through the gas jet (24) and out the gas orifice (30). As the gas passes through the space (52) and out of the fluid orifice (58), it creates a vacuum in the space (52) which draws liquid from the fluid reservoir (14) through the collector flange liquid passageway (62) and the nozzle liquid passageway (50), the liquid being drawn into the air stream passing through the orifice (58). The liquid is nebulized as a result of entering the high velocity air stream and is further nebulized when it impinges upon the diffuser (80). The resulting aerosol impinges upon the first and second baffles (71) and the annular flange (76), causing larger droplets to coalesce and fall back to the reservoir (14), while droplets of the proper size (88) remain suspended in the air and pass around the first and second baffles (71,74) and are discharged through the aerosol outlet (66) for inhalation by a patient.

The continuous flow adaptor (16) includes a cylindrical side wall (90) having male threads (92) surrounding an open top (94) and an annular collar (96) having female threads (98) therein surrounding an open bottom (100). As best seen in FIG. 3, the male threads (92) are configured to engage the female threads (68) of the nebulizer top (12) while the female threads (98) are configured to engage the male threads (38) of the reservoir bottom. A V-shaped annular channel (102) in the top of the side wall (90) nestingly receives the V-shaped annular protrusion (84) of the reservoir top (12) while a V-shaped annular flange (104) at the bottom of the side wall (90) is nestingly received within the V-shaped annular channel (42) of the reservoir bottom (14).

Figure 4:
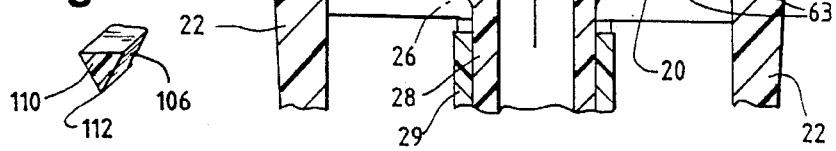
FIG. 4 is a cross-section of an adaptor diffuser support rib taken along line 4—4 of FIG. 1.

Three ribs (106) are circumferentially spaced at 120° intervals extend inwardly and downwardly from the adaptor side wall (90) to suspend an adaptor diffuser (108) at the center of the adaptor (16). As best seen in FIG. 4, the ribs 106 have a triangular cross-section (110) with the apex (112) of the triangle directed downward toward the spray nozzle (46).

A conduit (114) having a lumen or orifice (116) extends through the side wall (90) of the adaptor (16) to allow for fluid communication between the interior of the adaptor (16) and a fluid supply (not shown) outside of the adaptor 16 as indicated by the arrow (117). At the distal end of the conduit (114) is a luer connector (118) for connection to a supply line of a fluid supply (not shown).

As seen in FIG. 3, with the continuous flow adaptor (16) threadably engaged between the reservoir bottom (14) and the nebulizer top (12), a fluid seal is formed between the nebulizer top (12) and the reservoir bottom (14) by the cooperating V-shaped annular flange and channel structures (104,42) and (84,102), respectively. In a preferred embodiment, each of the V-shaped annular flanges (104,42) and the V-shaped annular channel (84,102) have textured or "frosted" surfaces (119) to further facilitate formation of a fluid seal. The male threaded top (102) and female threaded bottom (104) of the continuous flow adaptor (16) ensure that the adaptor is not put in upside down. Furthermore, the adaptor diffuser (108) is positioned the selected distance (85) of 0.022 inches from the fluid orifice (58) to ensure proper liquid droplet size for delivery to the lungs of a patient. With the adaptor so installed, fluid from a fluid supply can be continuously supplied to the reservoir (14) to replenish the liquid (120) in the reservoir (14) so that the nebulizer (14) may be continuously operated.

The continuous nebulizer adaptor disclosed herein allows for continuous supply of fluid to a nebulizer reservoir without having to disconnect the nebulizer from an inhalation circuit. Furthermore, the nebulizer adaptor allows for expedient modification of a conventional fixed volume nebulizer into a continuous flow nebulizer. In this manner, the continuous flow adaptor allows hospitals to stock only a single type of nebulizer for both continuous flow and fixed volume applications, thus decreasing hospital inventory requirements, thereby decreasing inventory costs and demands on storage space. Furthermore, the nebulizer adaptor eliminates the prior art requirement of a bulky fluid inlet stem fixed to the nebulizer reservoir, therefore decreasing the possibility of breakage of the stem, as well as decreasing the size of the nebulizer, thus decreasing packaging, transportation and storage costs of the nebulizer.

We claim:

1. A continuous flow adaptor for use in combination with a nebulizer having a reservoir bottom, a nebulizer top defining an aerosol outlet and means releasably connecting the reservoir bottom and the nebulizer top, the reservoir bottom further including nebulizing means having an outlet for providing an aerosol to the aerosol outlet, and means establishing fluid communication between the reservoir and the nebulizing means, the nebulizer top further including a diffuser spaced a selected distance from the nebulizing means outlet when the reservoir bottom and nebulizer top are connected by the first releasably connecting means, the continuous flow adaptor comprising:

a side wall defining first and second open ends and an adaptor interior between the first and second open ends;

an orifice in the side wall for allowing fluid communication with the adaptor interior;

means on the side wall of the adaptor for releasably connecting the orifice in fluid tight communication with a fluid supply;

means on the adaptor side wall for allowing cooperative engagement of the adaptor between a nebulizer top and a reservoir bottom;

an adaptor diffuser; and means for positioning the adaptor diffuser, the means for positioning being adapted to position the adaptor diffuser within the adaptor interior at a selected distance from a nebulizing means outlet with the adaptor cooperatively engaged between a nebulizer top and a reservoir bottom.

2. The continuous flow adaptor of claim 1 wherein the cooperatively engaging means on the adaptor comprises threads on the side wall proximate the first and second open ends adapted for threadably engaging a threads on a reservoir bottom and nebulizer top.

3. The continuous flow adaptor of claim 1 wherein the means on the side wall of the adaptor for releasably connecting comprises a luer connector on the side wall surrounding a periphery of the orifice.

4. The continuous flow adaptor of claim 1 wherein the first and second open ends are circular and the side wall is cylindrical.

5. The continuous flow adaptor of claim 1 further comprising a conduit having a distal end and a proximal end, the proximal end being fixedly connected to the side wall about the orifice.

6. The continuous flow adaptor of claim 5 wherein the means for connecting the orifice to the fluid supply comprises a luer connector on the distal end of the conduit.

7. The continuous flow adaptor of claim 1 wherein the positioning means comprises a plurality of ribs extending between the side wall and the diffuser.

8. The continuous flow adaptor of claim 7 wherein the plurality of ribs have a triangular cross-section with the apex of the triangle adapted to be directed a nebulizing means outlet with the adaptor connected between a nebulizer top and a reservoir bottom.

9. The continuous flow adaptor of claim 7 wherein the ribs are attached to the interior of the side wall proximate the first end with the ribs inclined toward the second end so that with the adaptor connected between a nebulizer top and reservoir bottom with the first end connected to a nebulizer top, a leading end of the adaptor diffuser is spaced a selected distance from a nebulizing means outlet and a nebulizer diffuser resides behind a trailing end of the adaptor diffuser and between the ribs.

10. The continuous flow adaptor of claim 1 wherein the cooperatively engaging means on the adaptor comprises male screw threads on the side wall proximate the first open end and female screw threads on the side wall proximate the second open end adapted for threadably engaging a threads on a reservoir bottom and nebulizer top.

* * * * *